(12) United States Patent
Hofberger (10) Patent No.: US 11,013,572 B2
(45) Date of Patent: May 25, 2021

(54) ADJUSTABLE TRAJECTORY GUIDE

(71) Applicant: Brainlab AG, Munich (DE)

(72) Inventor: Stefan Hofberger, Munich (DE)

(73) Assignee: BRAINLAB AG, Munich (DE)

( * ) Notice: Subject to any disclaimer, the term of this patent is extended or adjusted under 35 U.S.C. 154(b) by 473 days.

(21) Appl. No.: 15/573,746

(22) PCT Filed: Oct. 11, 2016

(86) PCT No.: PCT/EP2016/074320
§ 371 (c)(1),
(2) Date: Nov. 13, 2017

(87) PCT Pub. No.: WO2017/064050
PCT Pub. Date: Apr. 20, 2017

(65) Prior Publication Data
US 2018/0116753 A1    May 3, 2018

Related U.S. Application Data

(63) Continuation-in-part of application No. PCT/EP2015/073678, filed on Oct. 13, 2015.

(51) Int. Cl.
*A61B 90/11* (2016.01)
*A61B 90/50* (2016.01)
(Continued)

(52) U.S. Cl.
CPC .............. *A61B 90/11* (2016.02); *A61B 90/50* (2016.02); *A61B 34/10* (2016.02); *A61B 2017/3405* (2013.01)

(58) Field of Classification Search
CPC . A61B 90/11; A61B 90/50; A61B 2017/3405; A61B 34/10
See application file for complete search history.

(56) References Cited

U.S. PATENT DOCUMENTS 5,993,463 A    11/1999  Truwit et al.
6,290,196 B1 *  9/2001  Mayenberger ..... A61B 1/00149
                                                248/123.2
(Continued)

FOREIGN PATENT DOCUMENTS

DE    20200620006115 U    7/2006
DE    102007026721 A      5/2008
(Continued)

OTHER PUBLICATIONS

International Search Report and Written Opinion for PCT/EP2016/074320 dated Feb. 22, 2017.

*Primary Examiner* — Katherine M Rodjom
(74) *Attorney, Agent, or Firm* — Middleton Reutlinger (57) ABSTRACT

The present invention relates to an adjustable trajectory guide having a guide portion adapted to hold or provide a guiding for a medical instrument along a defined trajectory, and at least one adjustment section comprising: at least one elongated flexible beam member connected at its first end to the guide portion, and having at its second end a first engagement interface adapted to provide a connection to a support structure holding the trajectory guide; at least one second engagement interface which is movable relative to the at least one beam member and which is adapted to provide a connection to an actuator, at least one coupling member coupling the first end of the beam member to the second engagement interface, wherein the coupling member is capable of transmitting force and/or torque from the second engagement interface to the first end of the beam member. The present Invention further relates to a trajectory guide adjustment system comprising such trajectory guide, and corresponding method for aligning an elongated medical instrument utilizing such trajectory guide adjustment system.

14 Claims, 4 Drawing Sheets

(51) Int. Cl.
     *A61B 34/10*      (2016.01)
     *A61B 17/34*      (2006.01)

(56)           References Cited

U.S. PATENT DOCUMENTS

| | | |
|---|---|---|
| 2007/0055291 A1 | 3/2007 | Birkmeyer et al. |
| 2010/0234856 A1 | 9/2010 | Stoianovici et al. |

FOREIGN PATENT DOCUMENTS

| | | |
|---|---|---|
| EP | 2233256 B | 3/2011 |
| EP | 2392272 A | 12/2011 |
| EP | 2829239 B | 7/2015 |
| WO | 2015030671 A1 | 3/2015 |

\* cited by examiner

ADJUSTABLE TRAJECTORY GUIDE

TECHNICAL FIELD

The present invention relates to a trajectory guide which is utilized during a medical procedure to guide an elongated medical instrument to a target region.

SUMMARY

In medical procedures which require an elongated medical instrument such as a needle, a stimulation lead, a biopsy needle or a probe to be advanced through tissue along a predefined trajectory to a target region, trajectory guides are widely used. Such trajectory guides are usually connected to a support structure, such as a stereotactic arc, which holds the elongated instrument precisely rigidly to the support structure and therefore also to the patient, so that the instrument can be moved along its longitudinal axis only. The support structure is adjusted by a medical personnel so that the longitudinal axis of the elongated instrument conforms to the planned trajectory which runs through the target region. After fixing the support structure in the correct position, the elongated instrument is then advanced to the target region. For an accurate placement of the elongated instrument the longitudinal axis of the instrument has to be matched precisely to the planned trajectory, which requires a difficult and time consuming adjustment procedure of a support structure such as a stereotactic arc.

The present invention provides a trajectory guide which can be held by any suitable support structure, and that is adjustable relative to the support structure holding the trajectory guide. By doing so the longitudinal axis of the instrument held by the trajectory guide can be matched precisely to the planned trajectory.

The inventive trajectory guide is defined by the appended independent claims. Advantages, advantageous features, advantageous embodiments and advantageous aspects of the present invention are disclosed in the following and contained in the subject matter of the dependent claims. Different advantageous features can be combined in accordance with the invention wherever technical expedient and feasible. Specifically, a feature of one embodiment which has the same or a similar function to another feature of another embodiment can be exchanged with said other feature, and a feature of one embodiment which adds an additional function to another embodiment can in particular be added to said another embodiment.

The adjustable trajectory guide according to the present invention has a guide portion adapted to hold or provide for a medical instrument along a defined trajectory, and at least one adjustment section comprising:

- at least one elongated flexible beam member connected at it's first end to the guide portion, and having at it's second end a first engagement interface adapted to provide a connection to a support structure holding the trajectory guide;
- at least one second engagement interface which is movable relative to the at least one beam member and which is adapted to provide a connection to an actuator;
- at least one coupling member coupling the first end of the beam member to the second engagement interface, wherein the coupling member is capable of transmitting force and/or torque from the second engagement interface to the first end of the beam member.

In other words, the inventive trajectory guide comprises a guide portion which holds an elongated medical instrument so that the instrument can be moved relative to the guide portion along its longitudinal axis only, and an adjustment section coupling the guide portion to a first engagement interface via which the trajectory guide is attached to a support structure. The guide portion is coupled to the first engagement interface and therefore also to the support structure via one or more flexible beam members which can be deflected so as to move the guide portion together with the instrument relative to the support structure, allowing the longitudinal axis of the elongated instrument to be adjusted with respect to the support structure. Further, the trajectory guide comprises one or more coupling members which are connected to at least one of the beam members and which are used to apply force and/or torque on the beam members, which in turn causes the beam member(s) to bend or at least move. Each of the coupling members further comprises an interface connecting the coupling member to an actuator by means of which the beam member(s) can be flexed. Further, the beam member(s) themselves may comprise an interface via which it is/they are connected to the support structure or even to a further actuator employed to move the beam member with respect to the support structure, thereby allowing further adjustment of the guide portion with respect to the support structure.

The adjustable trajectory guide may further comprise at least one pair of coupling members which act on the first end of at least one beam member in an opposed manner, and which are in particular coupled to the same second engagement interface. With each pair of coupling members acting in an opposed manner, the beam member can be flexed in two opposed directions, which will double the possible scope of adjustment. In case the two opposed coupling members are coupled to one and the same engagement interface, it is possible to cause the beam member to bend in two opposed directions by employing only one actuator.

Further, the trajectory guide may have a symmetrical shape, with the longitudinal axis of the beam member being the symmetrical axis. With regard to the coupling members, a symmetrical shape of the trajectory guide will cause the beam member to bend in the two opposite directions in exactly the same manner, possibly caused by one single actuator which may act in two opposite directions.

Further, the at least one beam member may have at least one dedicated direction of flexibility. This can be achieved by a suitable cross sectional shape of the beam member providing an increased stiffness of the beam member in any direction which differs from the one or more dedicated bending directions. In the context of the at least one flexible beam member, the term "flexible" may on the one hand mean that a beam member may have a main body portion that is deformable itself, i.e. that will change its shape, particularly will bend or flex upon appliance of an external force. On the other hand however, a "flexible" beam member may also be a beam member with a relatively unflexible body portion that will maintain its shape at least sectionwise, but which is provided with one or more flexible sections or hinges that allow the beam member to deflect with respect to other structures it is attached to via the flexible sections or hinges.

The inventive trajectory guide may further comprise at least one spacer between a beam member and a coupling member, which is adapted to maintain a clearance between the beam member and the coupling member. Such spacers will prevent the coupling members from any unintended deflection with respect to the beam member that may result in an increased amount of force or torque that has to be applied on the beam member for a certain amount of flexion.

The spacers further prevent any unintended movement of the coupling members with respect to the beam member which may result in an unintended deflection of the guide portion. The spacers also provide a certain guiding for the coupling members while they transmit force and/or torque from the actuators to the beam member.

Further, at least one coupling member may be connected to a beam member at an acute angle at the beam member's first end. This results in a rather prominent position of the guide portion with respect to the trajectory guide, which in turn allows a free and unobstructed access to the medical instrument held by the guide portion.

It is conceivable that at least one second engagement interface and the guide portion are provided at opposite sides of the trajectory guide, particularly with the beam member positioned between the second engagement interface and the guide portion. In other words, the guide portion, the beam member and the second engagement interface are arranged in line, with the at least one second engagement interface and the corresponding actuators positioned away from the guide portion. Again, this will result in a most prominent and accessible position of the medical instrument held by the guide portion.

The guide portion may have a third engagement interface adapted to provide a connection to a support structure holding the guide portion, the third engagement interface being provided at a location which is spaced from a location where a beam member of the adjustment section is connected to the guide portion. Assuming that the support structure holds the third engagement interface in a fixed spatial position (i.e. fixed location and alignment), any motion of the beam member including a flexion of a beam member, will cause the point where the beam member is connected to the guide portion to move with respect to the point where the third engagement interface is connected to the guide portion. In the end, this will result in an altered alignment of the guide portion together with the longitudinal axis of the medical instrument.

In the alternative, the trajectory guide may comprise two adjustment sections as described above, wherein the beam members of the two adjustment sections are connected to the guide portion at locations spaced apart from each other. Assuming that the two adjustment sections can be actuated independently from each other, the alignment of the guiding portion together with the longitudinal axis of the medical instrument can be varied in an arbitrary manner over a wide range.

Even though it is conceivable that the two adjustment sections are connected to the guide portion at arbitrary positions, it is preferred to provide two, particularly two identical adjustment sections arranged relative to each other in a congruent, particularly in a symmetrical manner. This will not only allow for simplifying the manufacturing process of the trajectory guide, but again also allows for a prominent position of the guide portion.

It is further conceivable that at least one, preferably both adjustment sections are connected to the guide portion via joints, in particular flexible film joints. Such joints will provide for a determined movement of the guide portion with respect to the corresponding adjustment section, wherein the movement is restricted to the degree(s) of freedom allowed by the joint(s). Any type and number of joints may be provided for the connection between an adjustment section and the guide portion. In a specific embodiment, each of the adjustment sections may be connected to the guide portion via a pair of flexible film joints that each allow for a rotational degree of freedom and which, for each adjustment section, are aligned perpendicularly relative to each other.

It is further conceivable that the trajectory guide is made from a radiolucent material, particularly from a plastic material which is at least in part injection molded or extruded, specifically wherein the trajectory guide is formed as one integrally formed part. In case the trajectory guide is formed as one integrally formed part, the spacers which are hinged attached to the beam member and to a corresponding coupling member may be attached via at least one integral hinge. With the adjustment sections being arranged in a congruent manner as explained above, it is possible to form the trajectory guide at least in part by an extrusion process.

With the trajectory guide being made from a relatively cheap plastic material, it is conceivable to provide the trajectory guide as a disposable, particularly as a pre-sterilized and packaged product. In this case, the trajectory guide may be attached to the support structure prior to a medical procedure, and can be discarded after use, so that no additional sterilization process is necessary.

A further aspect of the present invention relates to a trajectory guide adjustment system, comprising:
  an adjustable trajectory guide as explained herein;
  a support structure adapted to hold the trajectory guide in a defined spatial position;
  at least one first actuator connected to the first engagement interface and configured to move the trajectory guide relative to the support structure, particularly in a translational motion; and
  at least one second actuator connected to a corresponding second engagement interface, and configured to move the corresponding second engagement interface relative to the at least one beam member, particularly in a translational motion.

The support structure may be any structure that is suitable to hold the trajectory guide in a defined spatial position with respect to the patient. Since the inventive trajectory guide is adjustable to a certain degree by itself, it is not even necessary to adjust the support structure in a position where the longitudinal axis of the instrument held by the guide portion of the trajectory guide precisely matches the pre-defined trajectory. It is rather sufficient for the support structure to rather "coarsely" position the instrument with respect to the planned trajectory, whereupon the adjustable trajectory guide is employed to transfer the instrument from the "coarse" position into a position which precisely matches the trajectory. In this respect, it is conceivable to provide an articulated arm of any suitable type as a support structure which holds the trajectory guide at a fixed spatial position with respect to the patient.

The trajectory guide adjustment system further comprises at least one first actuator and at least one second actuator for causing a fine-adjustment of the guide portion. At least one of the first and/or the second actuator may be a linear motor.

It is further conceivable that the at least one second engagement interface of the trajectory guide is moved relative to the beam member in a direction which is perpendicular to the direction the trajectory guide is moved relative to the support structure. This means that the actuator, particularly the linear motor for moving the beam member relative to the support structure acts in a direction which is perpendicular to the direction another actuator, particularly another linear motor acts on the second engagement interface for causing the at least one beam member to flex.

A further aspect of the present invention relates to a computer implement method for aligning an elongated medical instrument with a planned trajectory, comprising the steps of:
  acquiring trajectory data describing the spatial position of a trajectory to a target region;
  acquiring instrument data describing the spatial position of a longitudinal axis of the medical instrument;
  determining, based on the trajectory data and the instrument data, alignment data describing a positional alteration of the instrument that is necessary for the longitudinal axis to match the trajectory;
  controlling, based on the alignment data, at least one actuator of the trajectory guide adjustment system as described herein.

The inventive method may employ a controller for controlling the actuators of the trajectory guide adjustment system, so that after the support structure has been brought into a "coarse" position, the actuators, if necessary, perform a precise adjustment of the instrument's spatial position to precisely match the longitudinal axis of the instrument to the planned trajectory.

Further aspects of the present invention relate to a program which, when running on a computer, causes the computer to perform the method steps of the method described herein and/or a program storage medium on which the program is start, in particular in a non-transitory form, and to a trajectory guide adjustment system comprising a computer on which such program is stored and/or run.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figures 1, 2, 3:
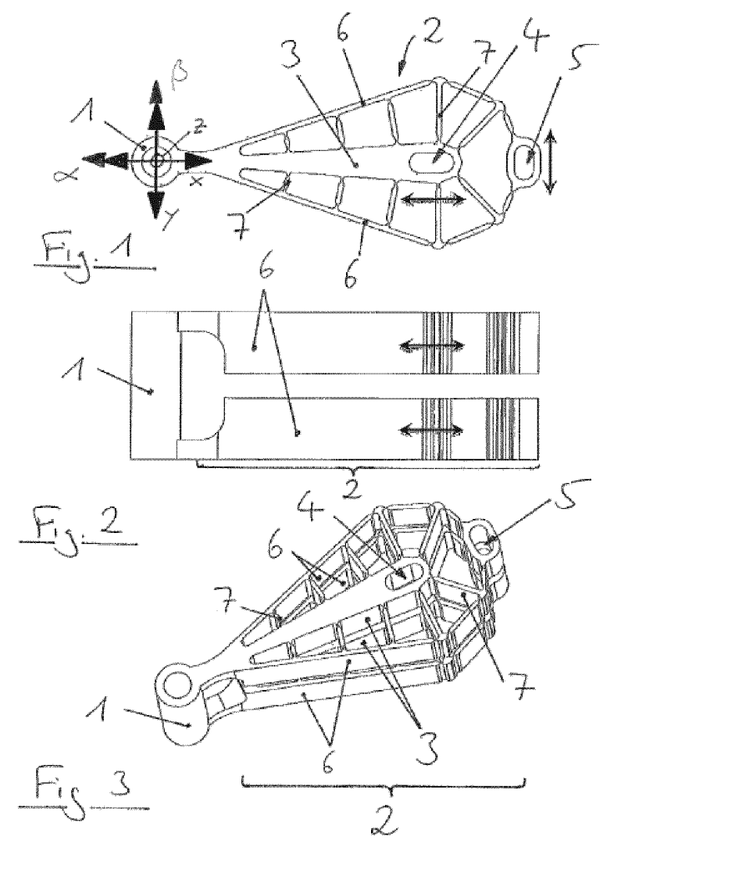
FIG. 1 a top view on a first embodiment of the inventive trajectory guide.
FIG. 2 a side view on the trajectory guide shown in FIG. 1.
FIG. 3 a perspective view on the trajectory guide shown in FIG. 1.

FIG. 1 shows a top view on a first embodiment of the inventive trajectory guide. At a first, left end of the trajectory guide a guide portion 1 is provided which is to hold a medical instrument (shown in FIG. 7) in a manner which allows the medical instrument to move only along its longitudinal axis. With the trajectory guide shown in FIG. 1, the longitudinal axis of the medical instrument would extend perpendicular to the drawing plane of FIG. 1 along the z-axis. The trajectory guide further comprises a first engagement interface 4 via which the whole trajectory guide can be attached to a support structure 9 (shown in FIGS. 6 and 7). The guide portion 1 is coupled to the first engagement interface 4 via a beam member 3 which is flexible in a direction (y-axis) perpendicular to its longitudinal axis (x-axis). Two counter-acting coupling members 6 are each connected to the beam member 3 in the vicinity of the guide portion 1, and are held at a predefined distance from the beam member 3 by several spacers 7 which are connected to both, the beam member 3 and the corresponding coupling member 6 via integral hinges. Both counter-acting coupling members 6 are attached at their other end to a common engagement interface 5 that allows an actuator 10 (shown in FIG. 7) to apply a force on the coupling members 6.

It becomes apparent from FIG. 1 that if the beam member 3 is moved in a x-direction by an actuator 10 engaging at interface 4, the guide portion 1 will also be moved along the x-axis. On the other hand, an actuator engaging at the second engagement interface 5 and moving in a y-direction will pull one of the coupling members 6 in a direction which is substantially perpendicular to the spacers 7, causing the beam member 3 to bend substantially along the y-axis. If the actuator 10 moves in the counter-direction, the beam member 3 will of course be bended together with the guide portion 1 in a counter-direction, as well. In order to ensure that the engagement interfaces 4, 5 move only in the direction of the corresponding actuators 10, the engagement interfaces 4, 5 have a rotationally non-symmetric shape.

It becomes apparent from FIG. 2 that the trajectory guide comprises two mirrored adjustment sections 2 which are connected to opposite ends of the guide portion 1.

In case the two adjustment sections 2 are moved relative to each other along the x-axis, the guide portion 1 will be rotated by an angle $\beta$, around the y-axis. In case the adjustment sections are moved by the same amount along the x-axis, the whole guide portion 1 will only be moved translationally along the x-axis.

In the same manner, the guide portion 1 will be moved translationally substantially along the y-axis in case both of the second engagement interfaces 5 are moved in the same direction parallel to the y-axis. In case the second engagement interfaces 5 are moved relative to each other and parallel to the y-axis, the beam members 3 will be bended in opposite directions, which will then cause the guide portion 1 to rotate by an angle $\alpha$ around the x-axis.

FIG. 3 shows a perspective view on the first embodiment of the inventive trajectory guide, which may be manufactured as an integral part by being injection molded.

Since both of the adjustment sections 2 of the trajectory guide are arranged relative to each other in a congruent manner, it is even possible to extrude the trajectory guide (along the z-axis), whereupon the two adjustment sections 2 may be separated from each other by a machining process.

Figure 4:
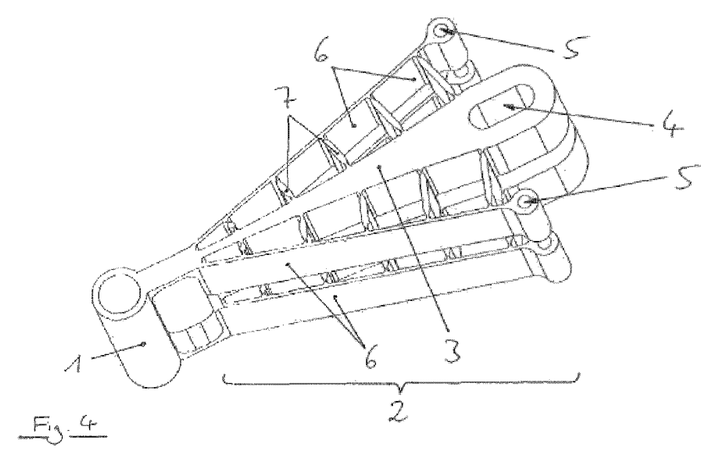
FIG. 4 a second embodiment of the inventive trajectory guide.

FIG. 4 shows a second embedment of the adjustable trajectory guide, which mostly corresponds to the first embodiment shown in FIGS. 1 to 3, except for the fact that each of the adjustment sections 2 comprises two separate second engagement interfaces 5, which may be connected to two corresponding engagement interfaces or actuators 10 of a support structure 9.

Figure 5:
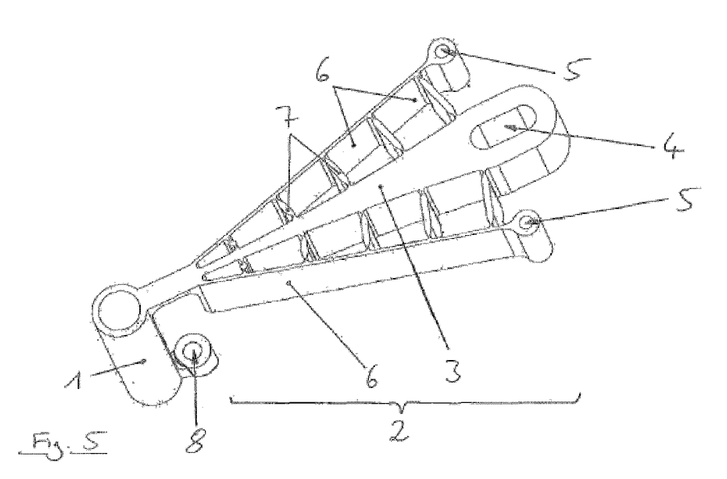
FIG. 5 a third embodiment of the inventive trajectory guide.

FIG. 5 shows a third embodiment of the inventive trajectory guide having only one single adjustment section 2. A third engagement interface 8 is provided at one end of the guide portion 1, opposite to the end the adjustment section 2 is connected to the guide portion 1. Imagining that the third engagement interface 8 is held in a fixed position with respect to the patient, moving the beam member 3 along the x-axis (shown in FIG. 1) will cause the guide portion 1 to rotate by an angle β around the y-axis. Bending the beam member 3 substantially along the y-axis will cause the guide portion to rotate by an angle α around the x-axis.

Figure 6:
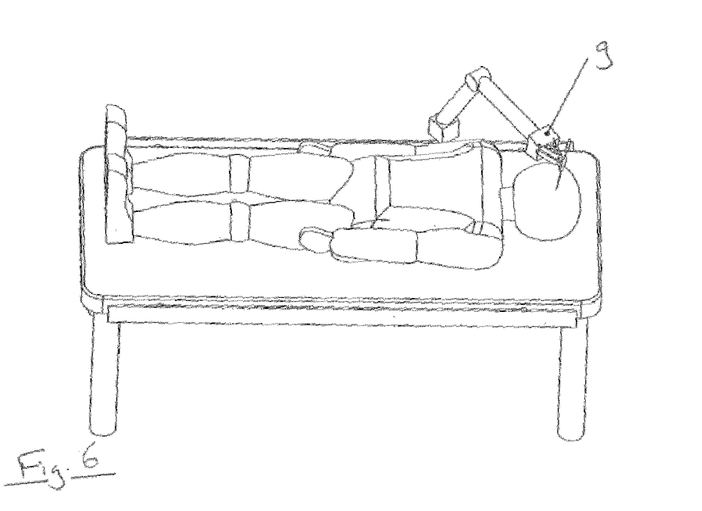
FIG. 6 the inventive trajectory guide held by a support structure in a surgical environment.
Figure 7:
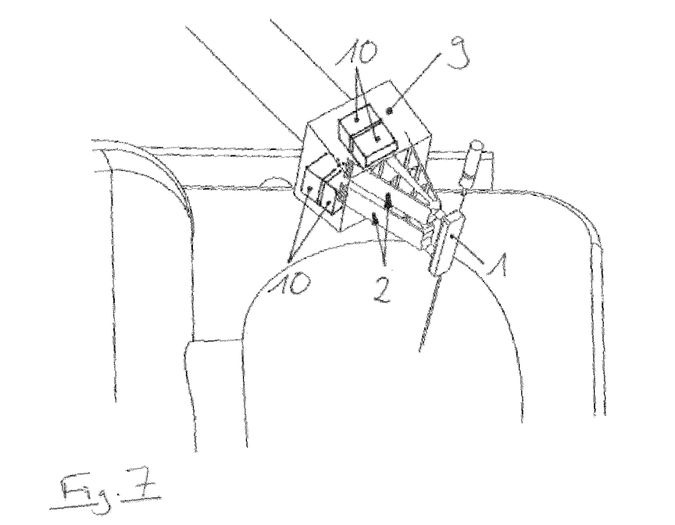
FIG. 7 a detailed view on the trajectory guide held by a support structure as shown in FIG. 6.

FIGS. 6 and 7 show a possible application of the inventive trajectory guide in a surgical environment. The inventive trajectory guide is held at a desired position with respect to a patient by an articulated arm having at its end a head 9 to which the trajectory guide is coupled. Head 9 comprises four actuators 10, one pair of the actuators 10 acting on one upper adjustment section 2, and the other pair of the actuators 10 acting on the other lower one of the adjustment sections 2.

With the adjustable trajectory guide provided at the head 9 of the articulated arm, the elongated axis of the instrument held by the guide portion 1 can be precisely matched to a predefined trajectory that runs through a target region, even if the articulated arm cannot be adjusted in a manner which is sufficiently precise to match the longitudinal axis of the instrument with respect to the desired trajectory.

The inventive trajectory guide therefore provides high accuracy in achieving and maintaining an alignment of the instrument axis with the target trajectory due to the playthree design of the trajectory guide. Even though the guide portion 1 is held at a prominent position with respect to the support structure 9, the trajectory guide may even serve as a drill-guide due to its stiffness. Since the trajectory guide may be made from a plastic material, artefact free X-rayimages or CT-images are possible due to the radiolucent properties of the trajectory guide. This also allows the trajectory guide to be provided as a pre-sterilized disposable article. However, the trajectory guide may also be adapted to be sterilized as a reusable article.

Figure 8:
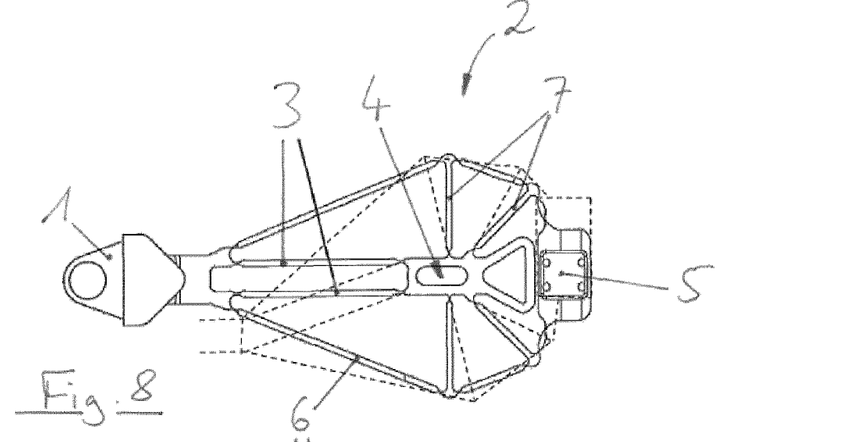
FIG. 8 a top view on a fourth embodiment of the inventive trajectory guide.
Figures 9, 10:
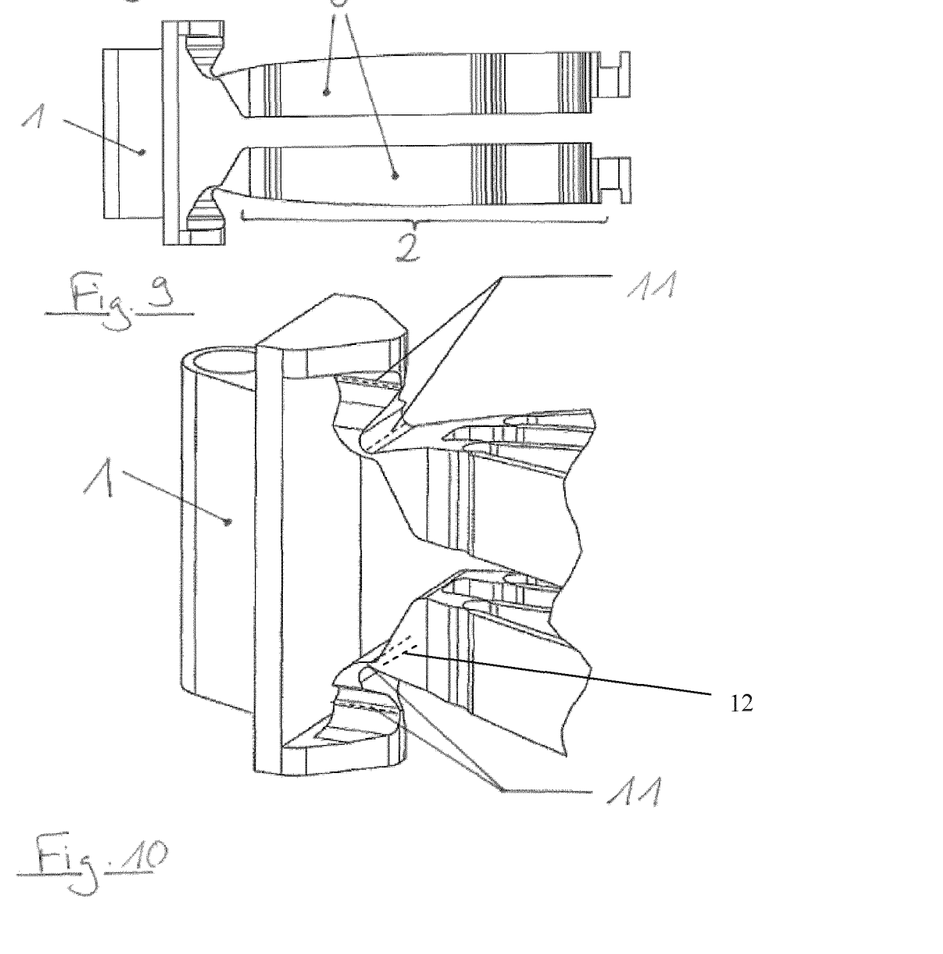
FIG. 9 a side view on the trajectory guide shown in FIG. 8.
FIG. 10 a perspective view on the trajectory guide shown in FIG. 8.

FIGS. 8 to 10 show a fourth embodiment of the inventive trajectory guide. Just like the first embodiment shown in FIGS. 1 to 3, the fourth embodiment has a guide portion 1 that is to hold a medical instrument with respect to a first and a second engagement interface 4, 5.

A first major difference to the first embodiment is that the trajectory guide comprises two beam members 3 for each adjustment section 2, each of the beam members 3 having a dimensionally stable body portion. In order to still allow for a movement of the guiding portion with respect to the engagement interfaces 4 and 5, each of the beam members 3 is connected to the guide portion 1 on the one hand and to the engagement interfaces 4, 5 on the other hand via flexible film joints (as seen in FIG. 8). With the two beam members 3 being arranged in parallel, an external force applied via a corresponding coupling member 6 will cause the guide portion 1 to move relative to the engagement sections 4, 5, thereby substantially maintaining its spatial orientation with respect to the engagement sections 4, 5. This will become apparent by looking at FIG. 8 showing a deflected state of the trajectory guide in broken lines.

A second major difference to the first embodiment shown in FIGS. 1 to 3 can be seen in FIG. 10. Each one of the two adjustment sections 2 is connected to the guide portion 1 via two film-joints 11 that each allow for a rotational degree of freedom, and which are aligned in a perpendicular manner relative to each other. The arrangement of two perpendicular film-joints 11 for each of the adjustment sections 2 lead to a precise and predictable movement of the guide section 1 with respect to the rest of the trajectory guide. To compensate for variations in the vertical distance between the film joints 11 (as seen in FIG. 9), caused by a relative motion between the upper and the lower adjustment sections 2, either the upper or the lower adjustment section 2 may be provided with two adjacent film joints 11 that run parallel to each other, for example perpendicularly to the plane of projection of FIG. 9.

The invention claimed is:

1. An adjustable trajectory guide having a guide portion adapted to hold or provide a guiding for a medical instrument along a defined trajectory, and at least one adjustment section comprising:
    at least one elongated flexible beam member connected at its first end to the guide portion, and having at its second end a first engagement interface adapted to provide a rigid connection to a support structure holding the trajectory guide;
    at least one second engagement interface which is movable relative to the at least one beam member and which is adapted to provide a connection to an actuator;
    at least one pair of coupling members acting on the first end of the beam member in an opposed manner and coupling the first end of the beam member to the at least one second engagement interface, wherein the at least one pair of coupling members is capable of transmitting force and/or torque from the at least one second engagement interface to the first end of the beam member, thereby causing the beam member to flex relative to the first engagement interface of the beam member.

2. The trajectory guide of claim 1, wherein the at least one pair of coupling members are coupled to the same second engagement interface.

3. The trajectory guide of claim 1, having a symmetrical shape, with the longitudinal axis of a beam member being the symmetrical axis.

4. The trajectory guide of claim 1, wherein the elongated flexible beam member has at least one dedicated direction of flexibility.

5. The trajectory guide of claim 1, further comprising at least one spacer between the elongated flexible beam member and the at least one pair of coupling members, which is adapted to maintain a clearance between the beam member and the at least one pair of coupling members.

6. The trajectory guide of claim 1, wherein at least one coupling member and the elongated flexible beam member are connected to each other at an acute angle at the elongated flexible beam member's first end.

7. The trajectory guide of claim 1, wherein the at least one second engagement interface and the guide portion are provided at opposite sides of the trajectory guide, with at least one beam member positioned between the at least one second engagement interface and the guide portion.

8. The trajectory guide of claim 1, wherein the guide portion has a third engagement interface adapted to provide a connection to a support structure holding the guide portion, the third engagement interface being provided at a location which is spaced from a location where the beam member of the at least one adjustment section is connected to the guide portion.

9. The trajectory guide of claim 1, comprising two adjustment sections, wherein the beam members of the two adjustment sections are connected to the guide portion at locations spaced from each other.

10. The trajectory guide of claim 9, wherein the two adjustment sections are arranged relative to each other in a symmetrical manner.

11. The trajectory guide of claim 1, made from a radiolucent material wherein the trajectory guide is formed as one integrally formed part.

12. A trajectory guide adjustment system, comprising:

an adjustable trajectory guide according to claim 1; and a support structure adapted to hold the trajectory guide in a defined spatial position;

at least one first actuator connected to the first engagement interface and configured to move the trajectory guide relative to the support structure in a translational movement; and at least one second actuator connected to a corresponding second engagement interface, and configured to move the corresponding second engagement interface relative to the beam member in a translational movement.

13. The trajectory guide adjustment system according to claim 12, wherein the at least one first actuator and/or the at least one second actuator is a linear motor, and/or wherein the at least one second engagement interface is moved relative to the beam member in a direction which is perpendicular to the direction the trajectory guide is moved relative to the support structure.

14. An adjustable trajectory guide, comprising:
a first and a second adjustment section each having
   at least one elongated flexible beam member connected at its first end to a guide and having at its second end a first engagement interface;
   a first and a second coupling member extending from the guide to a second engagement interface, the beam member positioned between the first and second coupling member;
   wherein the first and second coupling member are adapted to transmit force and/or torque from the second engagement interface to the first end of the beam member, thereby causing the beam member to flex relative to the first engagement interface of the beam member;
   a first plurality of spacers extending outward from the beam member to the first coupling member and a second plurality of spacers extending outward from the beam member to the second coupling member;
   the second engagement interface movable relative to the beam member;
the second adjustment section connected to the guide below the first adjustment section.

* * * * *